United States Patent

Hu et al.

[11] Patent Number: 5,846,666
[45] Date of Patent: Dec. 8, 1998

[54] ELECTROLUMINESCENT DEVICES

[75] Inventors: Nan-Xing Hu, Oakville; Shuang Xie, Mississauga; Beng S. Ong, Mississauga; Zoran D. Popovic, Mississauga; Ah-Mee Hor, Mississauga, all of Canada

[73] Assignee: Xerox Corporation, Stamford, Conn.

[21] Appl. No.: 807,488

[22] Filed: Feb. 27, 1997

[51] Int. Cl.$^6$ .................................... H05B 33/12
[52] U.S. Cl. ................. 428/690; 428/704; 428/917; 428/213; 428/332; 428/411.1; 428/457; 313/502; 313/503; 313/504; 313/506; 544/226; 544/353; 546/10; 546/101; 548/108; 548/148; 548/156; 548/217; 548/219
[58] Field of Search ...................... 428/690, 704, 428/917, 457, 332, 213, 411.1; 313/502, 503, 504, 506; 544/226, 353; 546/10, 101; 548/108, 148, 156, 217, 219

[56] References Cited

U.S. PATENT DOCUMENTS

| | | | |
|---|---|---|---|
| 4,356,429 | 10/1982 | Tang | 313/503 |
| 4,539,507 | 9/1985 | VanSlyke et al. | 313/504 |
| 4,769,292 | 9/1988 | Tang et al. | 428/690 |
| 4,950,950 | 8/1990 | Perry et al. | 313/504 |
| 5,150,006 | 9/1992 | VanSlyke et al. | 313/504 |
| 5,456,988 | 10/1995 | Sano et al. | 428/690 |

FOREIGN PATENT DOCUMENTS

| | | |
|---|---|---|
| 5-214333 | 8/1993 | Japan . |
| 5-331460 | 12/1993 | Japan . |

*Primary Examiner*—Marie Yamnitzky
*Attorney, Agent, or Firm*—E. O. Palazzo

[57] ABSTRACT

An electroluminescent device comprised of a metal thioxinoid of the formula

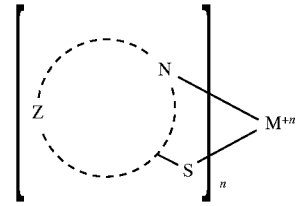

wherein M represents a metal; each n is a number of from 1 to 3; N is nitrogen, S is sulfur, and Z represents an aromatic moiety.

25 Claims, 2 Drawing Sheets

ELECTROLUMINESCENT DEVICES

PENDING APPLICATIONS

Illustrated in copending applications U.S. Ser. No. 707, 162, and U.S. Ser. No. 707,260, the disclosures of each being totally incorporated herein by reference, are certain electroluminescent devices. More specifically, disclosed in copending patent application U.S. Ser. No. 707,162 is a class of polynuclear aromatic tertiary amines for EL devices, which amines possess excellent thermal stability, and can be readily sublimed or evaporated under high vacuum to form stable thin-film hole injecting and transport layers. These polynuclear aromatic amines, by virtue of their large size and steric bulkiness, have exhibited excellent resistance towards crystallization when evaporated as thin films. They, therefore, can function as thermally and morphologically stable hole injecting and transporting components in EL devices.

Illustrated in copending applications U.S. Ser. No. 807, 489 are certain EL devices; U.S. Ser. No. 807,487 relates to a process for the preparation of Starburst amines, and U.S. Ser. No. 807,510 relates to photoconductive imaging members containing Starburst amines, each being filed concurrently herewith, and the disclosures of each application being totally incorporated herein by reference.

BACKGROUND OF THE INVENTION

This invention is generally directed to electroluminescent (EL) devices, and more specifically, to organic EL devices with in embodiments improved charge injection characteristics, low operation voltages, and thus improved device operation stability, and which devices utilize certain novel metal thioxinoid compounds as represented by Formula (I), including chelates of thioxine (also generally referred to as 8-quinolinethiol or 8-mercaptoquinoline), as the electron injecting and transporting component:

Formula (I)

wherein M represents a metal; each n is an integer, or number of from 1 to 3; S is sulfur, N is nitrogen, and Z represents the structural residue of the aromatic moiety including a heterocyclic structure with at least two fused aromatic rings. More specifically, Z is part of the structural residue that completes the aromatic system comprising, for example, quinoline, substituted quinoline, benzo{f}-quinoline, substituted benzo{f}-quinoline, benzo{h}quinoline, substituted benzo{h}quinoline, quinoxaline, 2-phenylbenzoxazole, 2-phenylbenzothiazole, and the like. The metals therein can be monovalent, divalent, or trivalent. Specific examples of metals include those which are known to form chelated compounds with thioxines, and preferably zinc, cadmium, gallium, and indium.

PRIOR ART

Electrooptical devices, such as cathode ray tubes (CRT's), are known. However, these devices are bulky and consume substantial amounts of energy. Furthermore, it is also difficult to manufacture a cost-effective distortion-free or low-distortion display based on CRT technology. Accordingly, there has been increased interest in developing compact flat-panel display devices which minimize space usage, and which can operate at low voltages of, for example, below 20 volts. Illustrative examples of CRT's include liquid crystal displays and others that are compatible with integrated circuit drivers, such as an array of thin film transistors as disclosed by T. S. Perry and P. Wallick in *IEEE Spectrum* 22 No. 7, 52 (1985); L. E. Tannas, Jr., *IEEE Spectrum* 23 No. 10, 37 (1986); and L. E. Tannas, Jr., *IEEE Spectrum* 26 No. 9, 34 (1989).

From the energy and space usage perspectives, particular attention has been devoted to developing energy-efficient flat-panel displays which are capable of providing a clear display without restrictive viewing angles. Currently, the majority of flat-panel display devices are liquid crystal based, however, these devices are encumbered with the problems of slow response and restrictive viewing angles. The EL display concept appears to offer a solution to these difficulties. Many of the current EL devices are based on inorganic materials, and they generally require high driving voltages. Organic EL devices, in contrast provide the advantage of lower driving voltages, however, they suffer from certain performance shortfalls, such as relatively short serviceable life and low electroluminescent efficiency. The organic EL devices of the present invention avoid or minimize these disadvantages by providing relatively long device life and high electroluminescent efficiency characteristics.

A simple organic EL device is generally comprised of a layer of organic luminescent material conductively sandwiched between an anode, typically comprised of a transparent conductor such as indium-tin oxide, and a cathode, typically a low work-function metal, such as magnesium, calcium, aluminum, or its alloy, with other metals. Under an applied electric field, positive charge carriers (holes) and negative charge carriers (electrons) are respectively injected from the anode and cathode into the luminescent layer where some of these oppositely charged carriers are recombined to form excitonic states which subsequently emit light. Early organic EL devices were constructed from a laminate of an organic luminescent material and electrodes of opposite polarity. These devices include single crystal materials, such as a single crystal anthracene, as the luminescent substance as illustrated, for example, in U.S. Pat. No. 3,530,325, the disclosure of which is totally incorporated herein by reference. These devices require excitation voltages on the order of 100 volts or greater. Subsequent modifications of device structure through incorporation of additional layers, such as charge injecting and charge transport layers, can lead to performance improvements. Illustrative examples of EL devices have also been disclosed in publications by Tang et al. in *J. Appl. Phys.*, vol. 65, pp. 3610–3616 (1989) and Saito et al. in *Mol. Cryst. Liq. Cryst*, vol. 253, pp. 125–132 (1994). Further known is the fabrication of organic EL devices such as those based on poly(p-phenylene vinylene), and disclosed by J. H. Burroughes et al., in *Nature* 347, 539 (1990).

Moreover, U.S. Pat. No. 4,950,950 to Perry et al. illustrates a multilayer EL device with silane hole transporting agents. U.S. Pat. No. 4,356,429 illustrates organic EL cells with a hole injecting porphyrinic zone. P. S. Vincett, W. A. Barlow, R. A. Hann and G. G. Roberts, *Thin Solid Films* 94, 171 (1982); R. H. Partridge, *Polymer* 24, 755 (1983); J. H. Burroughes et al., *Nature*, supra; D. Braun and A. J. Heeger, *Applied Physics Letters* 58, 1982 (1991); D. Braun and A. J. Heeger, *J. Electronic Materials* 20, 945 (1991); A. R. Brown et al., *Applied Physics Letters* 61, 2793 (1992); and J. Kido et al., *Applied Physics Letters* 59, 2760 (1991) disclose other organic EL compositions.

In one configuration, an organic EL device is comprised of a host organic polymer layer that supports hole injection from the anode and electron injection from the cathode, and is capable of emitting light in response to subsequent electron-hole recombination. The specific host organic polymer layer can further include a compound that facilitates hole injection and transport, a compound that facilitates electron injection and transport, and optionally, a fluorescent material capable of emitting light in response to recombination of holes and electrons.

In another configuration, an organic EL device may be comprised of certain dual organic layers in which one layer is adjacent to the anode supporting hole injection and transport, and another layer adjacent to the cathode supporting electron injection and transport. The recombination of charge carriers and subsequent emission of light occurs in one of these layers near the interface between the two layers. Optionally, a fluorescent dye can be added to one of the layers leading to the recombination of charge carriers and subsequent emission of light occurring in that compound.

In a further configuration, an EL device can be comprised of three separate layers, a certain hole transport layer, an emission layer, and a certain electron transport layer. These layers are laminated in sequence and are sandwiched as a whole between an anode and a cathode.

A method of fabricating organic EL devices with layered structures is by vacuum vapor deposition as illustrated in U.S. Pat. No. 4,769,292, the disclosure of which is totally incorporated herein by reference. Accordingly, EL materials for the charge transport and the luminescent layers are those that can be readily vacuum deposited as thin films. U.S. Pat. No. 4,356,429 describes EL devices containing a porphyrinic compound in the hole injecting layer between the luminescent zone and the anode, while in U.S. Pat. No. 4,539,507, the use of amines as a hole injecting layer to improve the light output efficiency of organic EL devices is disclosed. Specific amines illustrated in the '507 patent include bis(4-dimethylamino-2-methylphenyl)phenylmethane, N,N,N,-tri(p-tolyl)amine, 1,1,-bis(4-di-p-tolylaminophenyl)cyclohexane, and 1,1,-bis(4-di-p-tolylaminophenyl)-4-phenylcyclohexane. In addition, the use of tetraphenyldiamine as hole transport material in three-layer organic EL devices was described by C. Adachi et al. in *Jpn. J. Appl. Phys.*, Vol. 27, L269 to L271, 1988.

While the incorporation of a hole injecting and transporting component may lead to improved hole injection performance, there is a need for the design of electron injecting and transporting components which enhance electron injection. Electron injection has been more difficult than hole injection primarily because of the relatively large energy barrier between the n-contact and organic interface. In addition, while there are a number of known hole injecting and transporting materials which have been utilized in organic EL devices, organic electron injecting and transporting materials are not readily available. Specific examples of electron injecting and transporting materials which have been utilized in organic EL devices are disclosed in U.S. Pat. Nos. 3,172,862; 4,356,429; 4,539,507, and 5,150,006, the disclosures of each of these patents being totally incorporated herein by reference. Also known as electron injecting and transporting component is 2-(4-biphenylyl)-5-(4-tert-butylphenyl)-1,3,4-oxadiazole which is described by Adachi et al. in *Jpn. J. Appl. Phys.*, Vol. 27, L269 to L271, 1988. A class of electron injecting and transporting materials for organic EL devices are metal complexes of 8-hydroxyquinoline as described in the above-mentioned U.S. Pat. Nos. 4,539,507 and 5,150,006.

Primarily in view of the complexities and difficulties associated with the fabrication of layered organic EL devices, substantial efforts have been devoted to developing new charge injecting and transporting materials which improve EL device performance. Specifically, thus there is provided with the organic EL devices of the present invention in embodiments thereof a number of advantages, such as improved charge injection, low operation voltages, and enhanced electroluminescent efficiency, and which devices can be fabricated with an electron injecting and transporting component selected from a novel class of metal thioxinoid compounds.

The disclosures of each of the United States patents mentioned herein are totally incorporated herein by reference.

DESCRIPTION OF THE FIGURES

Illustrated in FIGS. 1, 2 and 3 are EL devices of the present invention.

SUMMARY OF THE INVENTION

Examples of objects of the present invention in embodiments thereof include:

It is an object of the present invention to provide organic EL devices with many of the advantages illustrated herein.

It is another object of the present invention to provide organic EL devices with improved electron injection characteristics.

In another object of the present invention there are provided improved organic EL devices which can be operated at low operating voltages of, for example, below 20 volts, such as from about 5 to about 19.5 volts, and high energy conversion efficiency, and enhanced thermal stability and operational stability.

A further object of the present invention is the provision of certain metal thioxinoid compounds as the electron injecting and transporting components for EL devices and the preparation thereof.

In still a further object of the present invention there is provided an organic EL device comprised of a supporting substrate of, for example, glass, an anode, a vacuum deposited organic hole injecting and transporting zone comprised of an aromatic tertiary amine, optionally containing a fluorescent component, a vacuum deposited electron injecting and transporting zone comprised of a metal thioxinoid compound, optionally containing a fluorescent component, and in contact therewith a low work function metal, such as magnesium and its alloy, as a cathode.

In yet another object of the present invention there is provided an organic EL device comprised of a vacuum deposited electron injecting and transporting zone comprised of an electron injecting metal thioxinoid compound and a known electron transporting component.

Further, in another object of the present invention there is provided an improved organic EL device comprised of a layer of a luminescent medium comprised of a hole transport component, an electron transport component of metal thioxinoid compound, and an optional fluorescent component, and which layer is sandwiched in between an anode and a cathode.

Another object of the present invention is the provision of polynuclear aromatic tertiary amine compounds of Formula (II) which possess excellent thermal stability, and can be readily vacuum deposited as thin films for use as hole transport components in organic EL devices, reference copending patent application U.S. Ser. No. 707,260, the disclosure of which is totally incorporated herein by reference.

Formula (II)

wherein $R^1$, $R^2$, $R^3$, $R^4$, and $R^5$ are aryl groups such as phenyl, tolyl, xylyl, naphthyl and the like, and $A^1$ and $A^2$ are biaryl groups such as biphenyl, bitolyl, and the like, or wherein aryl can include from 6 to about 24 carbon atoms, and biaryl can include from about 12 to about 48 carbon atoms.

In embodiments thereof the present invention relates to organic EL devices comprised of an electron injecting and electron transporting layer or zone, or layer comprised of certain novel metal thioxinoid compounds, a hole injecting and transporting layer or zone, or layer comprised of for example aromatic tertiary amine molecules, reference U.S. Pat. No. 4,265,990, the disclosure of which is totally incorporated herein by reference, polynuclear aromatic tertiary amine and the like, and which devices possess a number of advantages including superior electron injecting and electron transporting characteristics, low operating voltages, high electroluminescence efficiencies, improved thermal stability, long device life, and which devices can be readily fabricated using vacuum deposition techniques. The organic EL devices of the present invention, with polynuclear aromatic tertiary amines, exhibit improved thermal and operational stability, and excellent device durability at temperatures around and above 35° C. In embodiments, the electron injecting layer may inject electrons, transport electrons, or a combination thereof, and the hole injecting layer may inject holes, transport holes, or a combination thereof.

In embodiments, the present invention relates to organic EL devices comprised in the following order of an anode, an organic hole injecting and transporting zone or layer, an electron injecting and transporting zone or layer, and a cathode, wherein the electron injecting and transporting zone or layer is comprised of a metal thioxinoid compound as illustrated by Formula (I) herein. In embodiments, the present invention relates to an organic EL device comprised of a single luminescent layer comprised of an aromatic tertiary amine hole transport component, a metal thioxinoid electron injection component as described by Formula (I), and an optional fluorescent component, sandwiched between an anode and a cathode.

Formula (I)

wherein M represents a metal; each n is an integer of from 1 to 3; S is sulfur, N is nitrogen, and Z represents the structural residue of the aromatic moiety including a heterocyclic structure with at least two fused aromatic rings. More specifically, Z is part of the structural residue that completes the aromatic system comprising, for example, quinoline, substituted quinoline, benzo{f}-quinoline, substituted benzo{f}-quinoline, benzo{h}quinoline, substituted benzo{h}quinoline, quinoxaline, 2-phenylbenzoxazole, or 2-phenylbenzothiazole, and the like. The metals are known and can be monovalent, divalent, or trivalent. Specific examples of metals include those which are known to form chelated compounds with thioxines, and preferably such metals are zinc, cadmium, gallium, indium, and the like.

DESCRIPTION OF FIGURES

Figure 1:
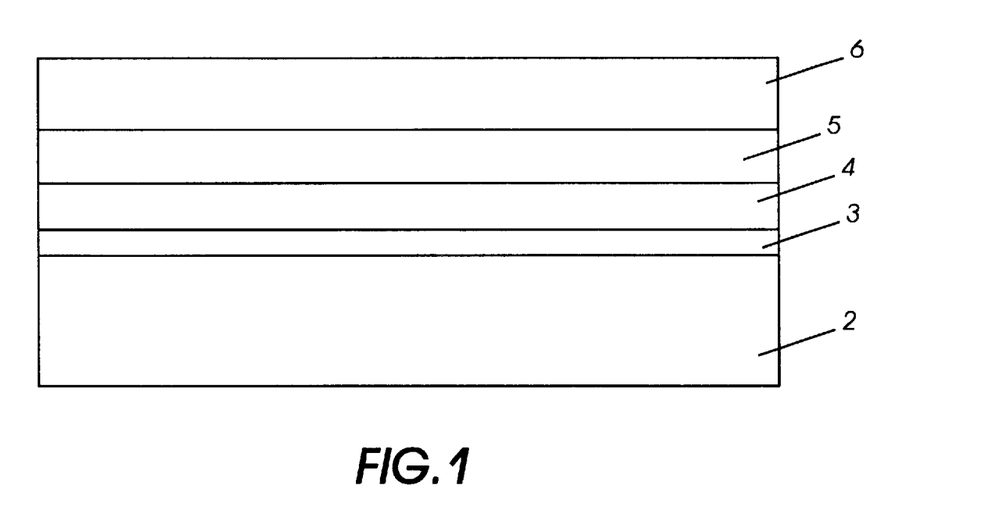
Figure 2:
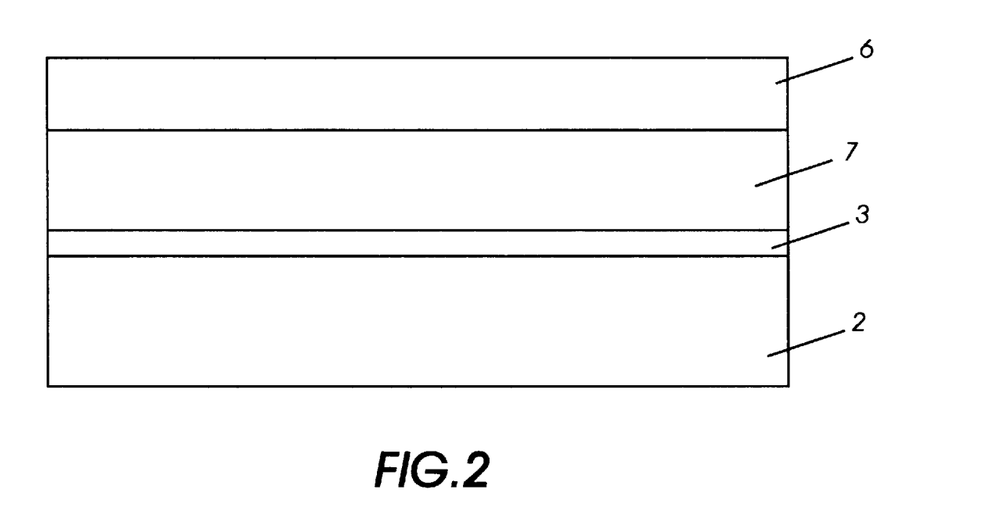
Figure 3:
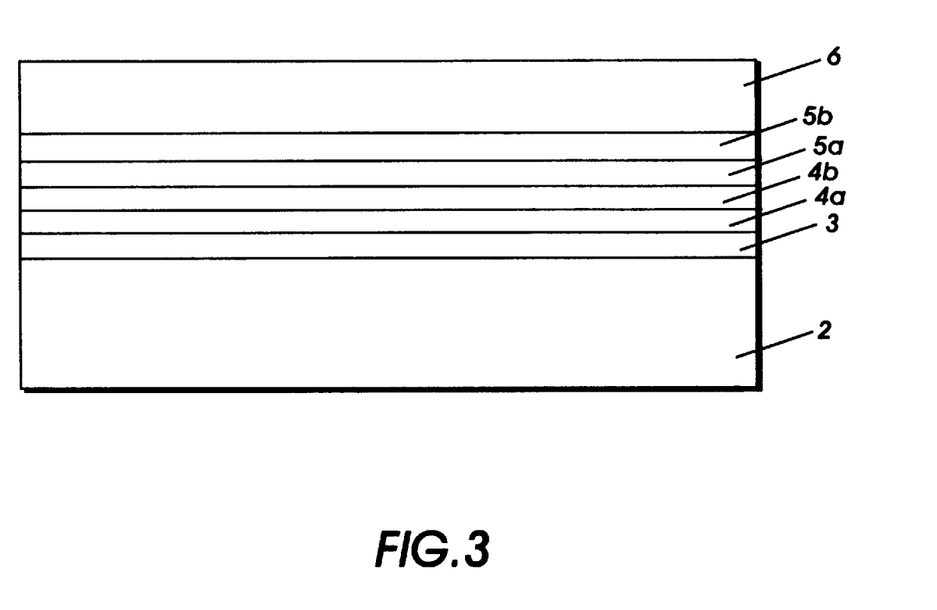

The embodiments of the present invention will be described in more detail with reference to the schematic diagrams of EL devices as depicted in FIGS. 1, 2 and 3.

FIG. 1 illustrates an EL device which comprises an organic light emitting diode comprised of a supporting substrate 2 of, for example, glass, an anode 3, a vacuum deposited organic hole injecting and transporting zone 4, a vacuum deposited electron injecting and transporting zone 5 comprised of at least one metal thioxinoid compound illustrated herein and of Formula (1), and in contact therewith a low work function metal as a cathode 6. In this EL device, a luminescent zone in which the electron-hole recombination takes place with subsequent light emission, encompasses the hole transport zone and/or the electron transport zone. Preferably, a fluorescent material, which is capable of emitting light subsequent to electron-hole recombination, may be added to the luminescent zone wherein the charge transport component functions as the host material.

More specifically, the device may include two zones, reference FIG. 3, that is in place of 4, 4a and 4b, and in place of 5, 5a and 5b, wherein 4a is the hole injecting layer, 4b is the hole transport layer, 5a is electron transporting and 5b is electron injecting; 4a and 4b together with 5 alone, or 5a and 5b together with 4 alone.

FIG. 2 illustrates another device configuration of the present invention comprising a single vacuum deposited luminescent zone 7, sandwiched between a cathode 6 and an anode 3 resting on a substrate 2. In embodiments of the present invention, the luminescent zone 7 is comprised of a hole injecting and transporting component, an electron injecting and transport component comprised of one metal thioxinoid compound of Formula (1), and a light emitting component.

Embodiments of the present invention include an electroluminescent device comprised of a novel metal thioxinoid of the formula Formula (I)

wherein M represents a metal; each n is a number of from 1 to 3; N is nitrogen, S is sulfur, and Z represents the structural residue of the aromatic moiety, and more specifically, Z is as indicated herein; an electroluminescent device comprising in sequence a supporting substrate, an anode, an organic hole injecting and transporting zone, an organic electron injecting and transporting zone, and a cathode, wherein said organic electron injecting and transporting zone is comprised of a layer of a metal thioxinoid of the Formula (I); an electroluminescent device comprising in sequence a supporting substrate, an anode, an organic hole injecting and transporting zone, an organic electron injecting and transporting zone, and a cathode, wherein said organic electron injecting and transporting zone is comprised of an electron transporting layer in contact with the hole injecting and transporting zone and, interposed between the electron transporting layer and the cathode, an electron injecting layer comprised of a metal thioxinoid of Formula (I); an electroluminescent device comprising a luminescent layer comprised of a hole injecting and transporting component, an electron injecting and transporting metal thioxinoid compound of Formula (I), and a fluorescent dye, and which layer is sandwiched, or situated between a cathode and an anode; and an EL device wherein the metal thioxinoid is selected from the group consisting of (1) bis(8-quinolinethiolato) zinc, (2) bis(8-quinolinethiolato)cadmium, (3) tris(8-quinolinethiolato)gallium, (4) tris(8-quinolinethiolato) indium, (5) bis(5-methylquinolinethiolato)zinc, (6) tris(5-methylquinolinethiolato)gallium, (7) tris(5-methylquinolinethiolato)indium, (8) bis(5-methylquinolinethiolato) cadmium, (9) bis(3-methylquinolinethiolato) cadmium, (10) bis(5-methylquinolinethiolato)zinc, (11) bis[benzo{f}-8-quinolinethiolato]zinc, (12) bis[3-methylbenzo{f}-8-quinolinethiolato]zinc, (13) bis[3,7-dimethylbenzo{f}8-quinolinethiolato]zinc, (14) bis(4-quinoxalinethiolato)zinc, (15) bis[2-(2-mercaptophenyl)benzothiazolate]zinc, and (16) bis[2-(2-mercaptophenyl) benzoxazolate]zinc.

Illustrative examples of supporting substrate include polymeric components, glass and the like, and polyesters like MYLAR™, polycarbonates, polyacrylates, polymethacrylates, polysulfones, quartz, and the like. Other substrates can be selected provided, for example, they are essentially nonfunctional and can support the other layers. The thickness of the substrate can be, for example, from about 25 to over 1,000 microns, from about 50 to about 1,000 microns, and the like, depending, for example, on the structural demands of the device.

The anode contiguous to the substrate in the organic EL devices of the present invention can be comprised of a metal, an alloy, an electroconducting compound or mixtures thereof, preferably with a work function equal to, or greater than 4 electron volts, for example from about 4 to about 7 electron volts. Specific examples of an anode, includes positive charge injecting electrodes such as indium tin oxide, tin oxide, zinc oxide, gold, platinum, or other materials including electrically conductive carbon and conjugated polymers such as polyaniline, polypyrrole, and the like. The thickness of the anode can range from about 10 nanometers to 1 micron with the preferred range being dictated by the optical constants of the anode material. One preferred range of thickness is from about 10 to about 200 nanometers.

The hole injecting and transporting zone 4 in the EL device of the present invention may be of a number of convenient forms. For example, the substrate may be comprised of one layer comprising one, two or more of hole transport components. In another preferred form, it may be laminately formed of a layer in contact with the anode containing a hole injecting component and a layer containing a hole transporting component interposed between the hole injecting layer and the electron injecting and transporting zone. The thickness of the hole injecting and transporting zone can be from 5 nanometers to 500 nanometers, and preferably from 10 nanometers to 100 nanometers. Any conventional materials which can inject and transport holes into the luminescent zone at a low electric field may be employed for forming the hole injecting and transporting zone. Preferred hole injecting and transporting materials include porphyrin derivatives and aromatic tertiary amines disclosed in U.S. Pat. No. 4,720,432, the disclosure of which is totally incorporated herein by reference.

Representative examples of phorphyrine derivatives are porphyrine; 1,10,15,20-tetraphenyl-21H,23H-porphyrin copper (II); copper phthalocyanine; copper tetramethyl phthalocyanine; zinc phthalocyanine; titanium phthalocyanine oxide; magnesium phthalocyanine; and the like.

Illustrative examples of aromatic tertiary amines are bis (4-dimethylamino-2-methylphenyl)phenylmethane, N,N,N-tri(p-tolyl)amine, 1,1-bis(4-di-p-tolylaminophenyl) cyclohexane, 1,1-bis(4-di-p-tolylaminophenyl)-4-phenylcyclohexane, N,N'-diphenyl- N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N', N'-tetra-p-tolyl-1,1'-biphenyl-4,4'-diamine, N,N'-di-1-naphthyl-N,N'-diphenyl-1,1'-biphenyl-4,4'-diamine, and the like.

Particularly preferred aromatic tertiary amines for the hole transporting layer or zone, and which amines may also inject holes, can be selected from those of polynuclear aromatic amines of Formula (II) illustrated herein. Specific examples include N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine; N,N-bis-[4'-(N-phenyl-N-m-chlorophenylamino)-4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m--tolylamino)-4-biphenylyl]-1-aminonaphthalene, and the like.

The electron injecting zone or layer, and which layer may also transport electrons, for the organic EL device of the present invention is comprised of a novel class of electron injecting and transporting components comprised of metal thioxinoid compounds as illustrated by Formula (I)

Formula (I)

wherein M represents a metal; each n is an integer of from 1 to 3; S is sulfur, N is nitrogen, and Z represents the structural residue of an aromatic moiety including a heterocyclic structure with at least two, and for example, up to about 10, fused aromatic rings. More specifically, Z is part of the structural residue that completes the aromatic system comprising, for example, quinoline, substituted quinoline, benzo{f}-quinoline, substituted benzo{f}quinoline, benzo{h}quinoline, substituted benzo{h}quinoline, quinoxaline, 2-phenylbenzoxazole, or 2-phenylbenzothiazole, and the like. The metals therein can be monovalent, divalent, or trivalent. Specific examples of metals include those which are known to form chelated compounds with thioxines, and preferably these metals include zinc, cadmium, gallium, indium, and the like.

Illustrative examples of metal thioxinoide compounds include (1) bis(8-quinolinethiolato)zinc, (2) bis(8-quinolinethiolato)cadmium, (3) tris(8-quinolinethiolato) gallium, (4) tris(8-quinolinethiolato)indium, (5) bis(5-methylquinolinethiolato)zinc, (6) tris(5- methylquinolinethiolato)gallium, (7) tris(5-methylquinolinethiolato)indium, (8) bis(5-methylquinolinethiolato) cadmium, (9) bis(3-methylquinolinethiolato)cadmium, (10) bis(5-methylquinolinethiolato)zinc, (11) bis[benzo{f}-8-quinolinethiolato]zinc, (12) bis[3-methylbenzo{f}-8-quinolinethiolato]zinc, (13) bis[3,7-dimethylbenzo{f}8-quinolinethiolato]zinc, (14) bis(4-quinoxaline thiolato)zinc, (15) bis[2-(2-mercaptophenyl)benzothiazolate]zinc, (16) bis[2-(2-mercaptophenyl) benzoxazolate]zinc, and the like.

The metal thioxinoid compounds can be prepared, for example, by the reaction of 8-quinolinethiol or its derivatives with the corresponding metal salts, followed by purification. In a typical reaction, thioxine and metal salt (½ equivalent amount of divalent metal salt or ⅓ equivalent amount of trivalent metal salt is used) are suspended in an aliphatic alcoholic solvent such as methanol or ethanol. With stirring, the suspension is treated with one equivalent amount of base, such as sodium hydroxide, potassium hydroxide, sodium ethoxide, and the like, at room temperature under an inert atmosphere. The precipitated solid is collected by filtration and further purified by sublimation. The structure and composition of the metal chelated compounds are confirmed by known analytical techniques such as ultraviolet-visible and infrared spectra, elemental analysis, and the like.

The electron injecting and transporting layer or zone may be a number of convenient forms. For example, it may be comprised of one layer comprising at least one metal thioxinoid compound and mixtures thereof with other known electron transport materials, and which mixture contains effective amounts of each component, for example from about 5 to about 95 percent of the metal thioxinoid complex, and from about 95 to about 5 weight percent of a known electron transporting material. Also, the electron injecting and transporting zone may be comprised of a layer in contact with the cathode containing an electron injecting metal thioxinoid compound, and a layer containing a known electron transporting compound interposed between the electron injecting layer and the hole injecting and transporting zone. Examples of known electron transport materials other than the metal thioxinoid chelate compounds include fused ring luminescent materials, such as anthracene, phenathrecene, pyrene, perylene, and the like, as illustrated by U.S. Pat. No. 3,172,862 the disclosure of which is totally incorporated herein by reference; butadienes such as 1,4-diphenylbutadiene and tetraphenylbutadiene, and stilbenes, and the like as illustrated in U.S. Pat. Nos. 4,356,429 and 5,516,577, the disclosures of each patent being totally incorporated herein by reference; optical brightness such as those disclosed by U.S. Pat. No. 4,539,507, the disclosure of which is totally incorporated herein by reference. Preferred electron transport materials are metal chelates of 8-hydroxyquinoline disclosed in U.S. Pat. Nos. 4,539,507; 5,151,629 and 5,150,006, the disclosures of which are totally incorporated herein by reference. Illustrative examples of the metal chelated compounds include tris(8-hydroxyquinolinate)aluminum (AIQ3), bis(8-hydroxyquinolinate)magnesium, tris(7-propyl-8-quinolinolato)aluminum, bis(2-methylquinolinolato) aluminum (III)-μ-oxo-bis(2-methyl-8-quinolinolato) aluminum(III), bis(2-methyl-8-quinolinolato)(phenolato) aluminum, bis(2-methyl-8-quinolinolato)(para-phenylphenolato)aluminum, and bis(2-methyl-8-quinolinolato)(2-naphthalolato)aluminum.

Various effective layer thicknesses can be selected for the EL devices as indicated herein, for example, and more specifically, the hole injecting and transporting layer, and electron injecting layer each are of a thickness of from about 50 to about 2,000, and preferably from about 400 to about 1,000 Angstroms. Other specific thicknesses may be selected and which thickness depends on a number of factors, such as the thicknesses of the other layers, the components for each layer, and the like.

It may be desirable to incorporate in the EL device charge transport layers a fluorescent dye to improve the device performance, reference the dyes of U.S. Pat. No. 4,769,292, the disclosure of which is totally incorporated herein by reference. Examples of fluorescent materials which can be employed in the EL devices of the present invention include those capable of being blended with the host material to form a common phase. Although any convenient techniques for dispersing the fluorescent agents in the host materials can be undertaken, the preferred technique is by vacuum vapor deposition wherein both the fluorescent agent and the host material can be simultaneously deposited. One preferred class of fluorescent materials is fluorescent dyes. Illustrative examples of fluorescent dyes are disclosed in U.S. Pat. No. 4,769,292 and include known compounds, such as coumarin dyes like 7-diethylamino-4-methylcoumarin, 4,6-dimethyl-7-ethylaminocoumarin, 4-methylumbelliferone, fluorescent 4-dicyanomethylene-4H-pyrans such as 4-(dicyanomethylene)-2-methyl-6(p-dimethylaminostyryl)-4H-pyran, and the like, polymethine dyes such as cyanines, merocyanines, complex cyanines and merocyanines, oxonals, hexioxonols, styryls, merostyryls, streptocyanines and the like, oxobenzanthracene dyes, xanthene dyes including rhodamine dyes such as [9-(o-carboxyphenyl)-6-(diethylamino)-3H-xanthen-3-yildene]diethyl ammonium, sulforhodamine B, and the like. Another specially preferred class of fluorescent materials is quinacridone dyes. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone and the like. Also, another preferred class of fluorescent materials are fused ring fluorescent dyes. Examples of the fused ring fluorescent dyes include perylene, rubrene, anthracene, coronene, N,N'-bis(2,6-di-t-butylphenyl)-3,4,9,10-perylene-bis (dicarboximide), and the like. The light emitting fluorescent material is present in an amount of, for example, from about 0.01 to about 10 weight percent, and preferably from about 1 to about 5 weight percent of the host transport layer.

The cathode 6 is formed by deposition thereof on the surface electron injecting layer 5. The cathode 6 can be comprised of any metal including any low work function metal useful for this purpose. The cathode can also be formed from a combination of a low work function metal and at least one other metal. A low work function metal is a metal having a work function equal to, or less than about 4.0 eV, for example from about 1 to about 4. The lower the work function of the metal, the lower the voltage required for electron injection into layer 5 or 7. The thickness of cathode 6 is, for example, from about 10 to about 5,000 Å.

Suitable low work function metals include alkaline metals, Group 2A, or alkaline earth metals, and Group III metals including rare earth metals and the actinide group metals. Lithium, magnesium and calcium are particularly preferred. Low work function metals exhibiting, for example, work functions in the range of from about 2.8 to about 4.0 eV are usually more stable than metals exhibiting lower, or higher work functions and are, therefore, preferred.

The cathode 6 may include a second metal for the purpose of increasing stability both during storage and operation. The second metal can be selected from any metal other than an alkaline metal. The second metal itself can be a low work function metal and suitable examples of the second metal include the examples of metals for the first metal having a work function of less than about 4 eV. As an alternative, the second metal can be selected from various metals having a work function of greater than about, for example, from about 4.0 to about 5.5 eV. The second metal includes elements more resistant to oxidation and therefore more commonly fabricated as metallic elements. The second metal contributes to the stability of cathode 6.

Suitable metals with a work function of 4 eV or greater include aluminum, indium, the Group IB metals, metals in Groups IV, V and VI and the Group VIII transition metals, particularly noble metals. Aluminum, indium, copper, silver, gold, tin, led, bismuth, tellurium and antimony are particularly preferred high work function second metals for incorporation into cathode 6.

A primary function of the second metal is to stabilize the first, low work function metal. A second function is to reduce sheet resistance of the cathode 6 as a function of the thickness of the cathode. This results in a very stable cathode 6 of acceptably low resistance and high electron injection efficiency. A third function of the second metal is to facilitate vacuum vapor deposition of the first metal.

Suitable proportions of the low work function metal to the second metal, preferably a metal having a work function greater than about 4.0 eV, may range from less than about 1 percent to about 99 percent by weight. The thickness of cathode 6 is of, for example, from about 10 to about 5,000 Å. The Mg:Ag cathodes of U.S. Pat. No. 4,885,211 constitute one preferred cathode construction. Another preferred cathode construction may be as illustrated in U.S. Pat. No. 5,429,884 in which the cathodes are formed of lithium alloys with other high work function metals such as aluminum and indium. The disclosures of each of the above patents are totally incorporated herein by reference.

Both anode 3 and cathode 6 of the organic EL devices of the present invention can be of any convenient forms. A thin, for example from about 200 to about 500 Angstroms, conductive layer can be coated onto a light transmissive substrate, for example a transparent or substantially transparent glass plate or plastic film. The EL device can include a light transmissive anode 3 formed of tin oxide or indium tin oxide coated on a glass plate. Also, very thin, for example from about 100 to about 400 Angstroms, light-transparent metallic anodes can be used, such as gold, palladium, and the like. In addition, transparent or semitransparent thin layers of conductive carbon or conjugated polymers such as polyaniline, polypyrrole, and the like can be used as anodes.

Any light transmissive polymeric film can be employed as the substrate. Further suitable forms of the anode 3 and cathode 6 are illustrated by U.S. Pat. No. 5,429,884.

Additionally in embodiments, the present invention is directed to organic layered EL devices comprised of a supporting substrate as illustrated herein, such as glass, a semitransparent layer of, for example, indium or tin oxide, an active single layer comprised of a polynuclear arylamine as illustrated herein, an emitter compound, the thioxinoid metal complex electron transport compound and a low work function electrode as the top layer; an EL device wherein the hole injecting and transporting layer is comprised of a mixture of an organic host material comprised of hole transport components, and a fluorescent dye having a band gap no greater than that of the host material and a reduction potential less negative than that of the host material, or wherein the electron transport layer is comprised of a blend of an organic host material comprised of electron transport, and a fluorescent dye having a band gap no greater than that of the host material and a reduction potential less negative than that of the host; an EL device wherein the fluorescent dye is selected from the group consisting of coumarin, dicyanomethylenepyrans, polymethine, oxabenzanthrane, xanthene, pyrylium, carbostyl, perylene, quinacridone, and fused aromatic ring fluorescent dyes; and an electroluminescent device wherein the supporting substrate is of a thickness of from about 25 to about 1,000 microns, the anode is of a thickness of from about 10 to about 500 nanometers, the luminescent layer is of a thickness of from about 5 to about 5,000 nanometers, and the cathode is of a thickness from about 5 nanometers to about 5 micrometers;

The following Examples are provided to further define various species of the present invention, it being noted that these Examples are intended to illustrate and not limit the scope of the present invention. Percentages are by weight unless otherwise indicated.

EXAMPLE I

Synthesis of bis(8-guinolinethiolate)zinc

In a 250 milliliter flask equipped with a magnetic stirrer were added quinolinethiol hydrochloride salt (5.0 grams, 25.3 mmol), ethanol (100 milliliters), and zinc chloride (1.75 grams, 12.8 mmol). The mixture was stirred at room temperature, about 25° C. throughout, under argon atmosphere for 10 minutes. To this mixture was added dropwise a 10 percent aqueous solution of sodium hydroxide (20 milliliters). After completion of the addition, the reaction mixture was heated to 50° C. (Centigrade) for 0.5 hour, and then allowed to cool to room temperature, about 25° C. throughout. The yellow precipitate resulting was collected by filtration, washed successively with water and methanol, and dried in a vacuum oven to afford 4.15 grams of bis(8-quinolinethiolate)zinc; m.p. 287.0° C.

EXAMPLE II

Synthesis of tris(8-guinolinethiolate)gallium

In a 250 milliliter flask equipped with a magnetic stirrer were added quinolinethiol hydrochloride salt (3.0 grams, 15.2 mmol), ethanol (50 milliliters), and gallium chloride (0.9 gram, 5.1 mmol). The resulting mixture was stirred at room temperature under an argon atmosphere for 10 minutes. To this mixture was added dropwise a 10 percent aqueous solution of sodium hydroxide (12 milliliters). After completion of the addition, the reaction mixture was heated to 50° C. for 1.0 hour and then allowed to cool to room temperature. The yellow precipitate resulting was collected by filtration, washed successively with water and methanol, and dried in a vacuum oven to afford 2.25 grams of tris(8-quinolinethiolate)gallium; m.p. 351.9.0° C.

EXAMPLE III

An organic EL device was prepared as follows:

1. An indium tin oxide, 500 Angstroms in thickness, (ITO) coated glass, about 1 millimeter in thickness for the glass, was cleaned with a commercial detergent, rinsed with deionized water and dried in a vacuum oven at 60° C. for 1 hour. Immediately before use, the glass was treated with UV ozone for 0.5 hour.
2. The ITO substrate was placed in a vacuum deposition chamber. The deposition rate and layer thickness were controlled by an Inficon Model IC/5 controller. Under a pressure of less than about 5×10$^{-6}$ Torr the hole transport compound, N,N'-diphenyl-N,N'-bis(3-methylphenyl)1,1'-biphenyl-4,4'-diamine (TBD), and rubrene were simultaneously evaporated from two independently electrically heated tantalum boats to deposit an 80 nanometers thick layer on the ITO glass. The deposition rates of the hole transport compound and rubrene were controlled at 0.6 nanometer/second and 0.03 nanometer/second, respectively.
3. Onto the hole transport layer 2 was deposited tris(8-quinolinethiolato)zinc at an evaporation rate of 0.6 nanometer/second to form an 80 nanometers, about 800 Angstroms, electron injecting and transporting layer.
4. A 100 nanometer magnesium silver alloy was then deposited at a total deposition rate of 0.5 nanometer/second onto the electron injecting and transporting layer by simultaneous evaporation from two independently controlled tantalum boats containing Mg and Ag, respectively. The typical composition was 9:1 in atomic ratio of Mg to Ag. Finally, a 200 nanometer silver layer was overcoated on the Mg:Ag cathode for the primary purpose of protecting the reactive Mg from ambient moisture.

The device as prepared above was retained in a dry box which was continuously purged with nitrogen gas. Its performance was assessed by measuring its current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

In testing, the device emitted yellowish green light with a peak emission at 565 nanometers and a maximum light intensity of 17,000 cd/cm$^2$ at 19.0 volts. The electroluminescent efficiency was measured to be 4.25 cd/A at a current density of 33 mA/cm$^2$, and the operating voltage at 33 mA/cm$^2$ was 9.2 volts.

EXAMPLE IV

An organic EL device was prepared in accordance with the procedure of Example III except that before the deposition of bis(8-quinolinethiolato)zinc, an 80 nanometer tris(8-hydroxyquinolinate)aluminum was additionally deposited onto the hole transport layer to form an electron transport layer. The device was completed by the deposition of bis(8-quinolinethiolato)zinc as the electron injecting layer followed by the deposition of a magnesium silver alloy as the cathode as described in Example III.

In light-voltage characteristic testing, the device emitted yellowish green light with a peak emission at 565 nanometers and a maximum light intensity of 24,000 cd/cm$^2$ at 17.0 volts. The electroluminescent efficiency was measured to be 5.69 cd/A at a current density of 33 mA/cm$^2$, and the operating voltage at 33 mA/cm$^2$ was 8.0 volts.

EXAMPLE V

An organic EL device was prepared in accordance with a modified procedure of Example III. On to a cleaned ITO substrate was deposited a 80 nanometer hole transport layer of N,N'-diphenyl-N,N'-bis(3-methylphenyl)-1,1'-biphenyl-4,4'-diamine, followed by deposition of a 80 nanometer electron injection and transport layer by simultaneous evaporation of bis(8-quinolinethiolato)zinc and rubrene from two independently controlled tantalum boats. The deposition rates of bis(8-quinolinethiolato)zinc and rubrene are controlled at 0.6 nanometer/second and 0.03 nanometer/second, respectively. The device was completed by deposition of a Mg:Ag alloy as the cathode as described in Example III.

In testing, (light-voltage characteristic testing throughout the Examples) the device emitted yellowish green light with a peak emission at 550 nanometers and a maximum light intensity of 10,160 cd/cm$^2$ at 17.0 volts. The electroluminescent efficiency was measured to be 2.05 cd/A at a current density of 33 mA/cm$^2$, and the operating voltage at 33 mA/cm$^2$ was 6.5 volts.

EXAMPLE VI

An organic EL device was prepared in accordance with a modification of the procedure of Example III. On to a cleaned ITO substrate was deposited an 80 nanometer hole transport layer of N,N'-di-1-naphthyl-N,N'-diphenyl-1,1'-biphenyl-4,4'-diamine, followed by deposition of a 80 nanometer electron injection and transport layer by simultaneous evaporation of bis(8-quinolinethiolato)zinc and N,N'-dimethyl-2,9-dimethylquinacridone from two independently controlled tantalum boats. The deposition rates of bis(8-quinolinethiolato)zinc and N,N'-dimethyl-2,9-dimethylquinacridone were controlled at 0.6 nanometer/sec and 0.006 nanometer/second, respectively. The device preparation was completed by deposition of a Mg:Ag alloy as the cathode as described in Example III.

In testing, the device emitted yellowish green light with a peak emission at 550 nanometers and a maximum light intensity of 12,500 cd/cm$^2$ at 19.0 volts. The electroluminescent efficiency was measured to be 3.05 cd/A at a current density of 33 mA/cm$^2$, and the operating voltage at 33 mA/cm$^2$ was 9.5 volts.

EXAMPLE VII

An organic EL device was prepared in accordance with the modified Example III process. On to a cleaned ITO substrate was deposited an 80 nanometer hole transport layer of N,N'-diphenyl-N,N'-bis(3-methylphenyl)-1,1'-biphenyl-4,4'-diamine, followed by deposition of an 80 nanometer electron injection and transport layer by simultaneous evaporation of tris(8-hydroxyquinolinate)aluminum and rubrene from two independently controlled tantalum boats. The deposition rates of tris(8-hydroxyquinolinate)aluminum and rubrene are controlled at 0.6 nanometer/second and 0.03 nanometer/second, respectively. The device was completed by deposition of an 80 nanometer bis(8-quinolinethiolato) zinc as the electron injecting layer and a magnesium silver alloy as the cathode as described in Example III.

In testing, the device emitted yellowish green light with a peak emission at 565 nanometers and a maximum light intensity of 12,300 cd/cm² at 15.0 volts. The electroluminescent efficiency was measured to be 2.58 cd/A at a current density of 33 mA/cm², and the operating voltage at 33 mA/cm² was 9.5 volts.

EXAMPLE VIII

An organic EL device was prepared in accordance with the procedure of Example III except that N,N-bis-[4'-(N-phenyl-N-m-tolylamino)4-biphenylyl]-m-toluidine was utilized in place of N,N'-diphenyl-N,N'-bis(3-methylphenyl)-1,1'-biphenyl-4,4'-diamine as the hole transport component.

In testing, the device emitted yellowish green light with a peak emission at 565 nanometers and a maximum light intensity of 18,250 cd/cm² at 18.0 volts. The electroluminescent efficiency was measured to be 4.35 cd/A at a current density of 33 mA/cm², and the operating voltage at 33 mA/cm² was 9.5 volts. The operational stability of the device was evaluated at 20° C. under a constant current density of 33 mA/cm². The initial light intensity was 1,450 cd/m², an intensity level that is in substantial excess of that required for practical application. The light intensity decreased slowly over time, and a 50 percent reduction in light intensity was observed after 250 hours of continuous operation. In addition, the device displayed no changes in the current-light intensity characteristics even after it was subjected to a temperature of 40° C. for 72 hours.

EXAMPLE IX

An organic EL device was prepared in accordance with the procedure of Example IV except that tris(8-quinolinethiolato)gallium was utilized in place of bis(8-quinolinethiolato)zinc.

In testing, the device emitted yellowish green light with a peak emission at 565 nanometers and a maximum light intensity of 11,000 cd/cm² at 19.5 volts. The electroluminescent efficiency was measured to be 1.35 cd/A at a current density of 33 mA/cm², and the operating voltage at 33 mA/cm² was 7.0 volts.

Other modifications of the present invention may occur to one of ordinary skill in this art subsequent to a review of the present application and these modifications, including equivalents thereof, are intended to be included within the scope of the present invention.

What is claimed is:

1. An electroluminescent device comprised of an anode, a cathode, and a metal thioxinoid of the formula wherein M represents a metal; each n is a number of from 1 to 3; N is nitrogen, S is sulfur, and Z is benzo{f}-quinoline, substituted benzo{f}-quinoline, benzo{h}quinoline, substituted benzo{h}quinoline, quinoxaline, 2-phenylbenzoxazole, or 2-phenylbenzothiazole.

2. A device in accordance with claim 1 wherein the metal thioxinoid is selected from the group consisting of (11) bis[benzo{f}-8-quinolinethiolato]zinc, (12) bis[3-methylbenzo{f}8-quinolinethiolato]zinc, (13) bis[3,7-dimethylbenzo {f}-8-quinolinethiolato]zinc, (14) bis(4-quinoxalinethiolato)zinc, (15) bis[2-(2-mercaptophenyl)benzothiazolate]zinc, and (16) bis[2-(2-mercaptophenyl)benzoxazolate]zinc.

3. An electroluminescent device in accordance with claim 1 comprising in sequence a supporting substrate, an anode, an organic hole injecting and hole transporting layer or zone, an organic electron injecting and electron transporting layer or zone, and a cathode, wherein said organic electron injecting and transporting zone or layer is comprised of said metal thioxinoid.

4. A device in accordance with claim 3 wherein the hole injecting and transporting zone is comprised of polynuclear arylamines as represented by the following formula wherein $R^1$, $R^2$, $R^3$, $R^4$, and $R^5$ are aryl, and $A^1$ and $A^2$ are biaryl.

5. A device in accordance with claim 3, wherein the hole injecting and transporting zone is comprised of aromatic tertiary amines as represented by the following formula wherein P is a phenylene group; n is an integer of from 1 to 4; and $R^6$, $R^7$, $R^8$, and $R^9$ are aryl groups independently selected from the group consisting of phenyl groups, and naphthyl groups.

6. A device in accordance with claim 3 wherein said hole injecting and transporting layer is comprised of a mixture of an organic host material comprised of hole transport components, and a fluorescent dye with a band gap no greater than that of said host material and a reduction potential less negative than that of said host material.

7. A device in accordance with claim 6 wherein said fluorescent dye is selected from the group consisting of coumarin, dicyanomethylenepyranes, polymethine, oxabenzanthrane, xanthene, pyrylium, carbostyl, perylene, quinacridone, and fused ring aromatic fluorescent dyes.

8. A device in accordance with claim 6 wherein said fluorescent dye is rubrene.

9. A device in accordance with claim 6 wherein the said fluorescent dye is present in an amount of from about $10^{-3}$ to about 10 mole percent, based on the moles of said host material.

10. The electroluminescent device of claim 3 wherein the substrate is a polymer, a metal, a semiconductor or glass.

11. The electroluminescent device of claim 3 wherein the anode is an indium tin oxide.

12. The electroluminescent device of claim 3 wherein the cathode is a layer of a plurality of metals, at least one of the said metals having a work function less than about 4 eV.

13. The electroluminescent device of claim 12 wherein said metal having a work function of less than about 4 eV comprises at least one alkaline metal, an alkaline earth metal, a rare earth metal, or a Group III metal.

14. The electroluminescent device of claim 3 wherein the supporting substrate is of a thickness of from about 25 to about 1,000 microns, the anode is of a thickness of from about 10 to about 500 nanometers, the hole injecting and transporting layer is of a thickness of from about 5 to about 500 nanometers, the electron injecting and transporting layer is of a thickness of from about 5 to about 500 nanometers, and the cathode is of a thickness of from about 5 nanometers to about 5 micrometers.

15. The electroluminescent device of claim 3 wherein the supporting substrate is of a thickness of from about 25 to about 1,000 microns, the anode is of a thickness of from about 10 to about 500 nanometers, and the cathode is of a thickness of from about 5 nanometers to about 5 micrometers.

16. A device in accordance with claim 1 wherein said metal is zinc, cadmium, gallium, or indium.

17. An electroluminescent device comprising a luminescent layer comprised of a hole injecting and transporting component, and an electron injecting and transporting metal thioxinoid compound of the following Formula, wherein M represents a metal; each n is a number of from 1 to 3; N is nitrogen, S is sulfur, and Z is benzo{f}-quinoline, substituted benzo {f}-quinoline, benzo {h}quinoline, substituted benzo{h}quinoline, quinoxaline, 2-phenylbenzoxazole, or 2-phenylbenzothiazole, and a fluorescent dye, and which luminescent layer is sandwiched between a cathode and an anode.

18. A device in accordance with claim 17 wherein the metal thioxinoid is selected from the group consisting of (11) bis[benzo{f}-8-quinolinethiolato]zinc, (12) bis[3-methylbenzo{f}-8-quinolinethiolato]zinc, (13) bis[3,7-dimethylbenzo{f}-8-quinolinethiolato]zinc, (14) bis(4-quinoxalinethiolato)zinc, (15) bis[2-(2-mercaptophenyl) benzothiazolate]zinc, and (16) bis[2-(2-mercaptophenyl) benzoxazolate]zinc.

19. A device in accordance with claim 17 wherein the hole injecting and transporting component is comprised of polynuclear arylamines as represented by the following formula wherein $R^1$, $R^2$, $R^3$, $R^4$, and $R^5$ are aryl, and $A^1$ and $A^2$ are biaryl.

20. A device in accordance with claim 17 wherein the hole injecting and transporting component is comprised of aromatic tertiary amines represented by the following formula wherein P is a phenylene group; n is an integer of from 1 to 4; and $R^6$, $R^7$, $R^8$, and $R^9$ are aryl groups independently selected from the group consisting of phenyl groups, and naphthyl groups.

21. The electroluminescent device of claim 17 wherein the cathode is comprised of a plurality of metals, at least one of the said metals possessing a work function greater than about 4 eV.

22. The electroluminescent device of claim 17 wherein the anode is comprised of conductive carbon, a conductive polypyrrole, or a conductive polyaniline.

23. A device in accordance with claim 3 wherein said metal is zinc, cadmium, gallium, or indium.

24. A metal thioxinoid of the formula:

wherein M represents a metal; each n is a number of from 1 to 3; N is nitrogen, S is sulfur, and Z is benzo {f}-quinoline, substituted benzo{f}-quinoline, benzo{h}quinoline, substituted benzo{h}quinoline, quinoxaline, 2-phenylbenzoxazole, or 2-phenylbenzothiazole.

25. A metal thioxinoid in accordance with claim 24 wherein said metal thioxinoid is selected from the group consisting of (11) bis[benzo{f}-8-quinolinethiolato]zinc, (12) bis[3-methylbenzo{f}-8-quinolinethiolato]zinc, (13) bis[3,7-dimethylbenzo{f}-8-quinolinethiolato]zinc, (14) bis(4-quinoxalinethiolato)zinc, (15) bis[2-(2-mercaptophenyl) benzothiazolate]zinc, and (16) bis[2-(2-mercaptophenyl) benzoxazolate]zinc.

* * * * *